(12) United States Patent
Amhamed et al.

(10) Patent No.: US 11,796,196 B2
(45) Date of Patent: Oct. 24, 2023

(54) ADSORPTION FILTER, VENTILATION SYSTEM AND HVAC SYSTEM HAVING THE SAME

(71) Applicant: Qatar Foundation for Education, Science and Community Development, Doha (QA)

(72) Inventors: Abdulkrem Amhamed, Doha (QA); Ahmed Sodiq, Doha (QA); Moazzam Khan, Doha (QA)

(73) Assignee: QATAR FOUNDATION FOR EDUCATION, SCIENCE AND COMMUNITY DEVELOPMENT, Doha (QA)

( * ) Notice: Subject to any disclaimer, the term of this patent is extended or adjusted under 35 U.S.C. 154(b) by 63 days.

(21) Appl. No.: 17/233,687

(22) Filed: Apr. 19, 2021

(65) Prior Publication Data
US 2021/0325064 A1    Oct. 21, 2021

Related U.S. Application Data

(60) Provisional application No. 63/012,597, filed on Apr. 20, 2020.

(51) Int. Cl.
| *B01D 53/04* | (2006.01) |
| *F24F 8/22* | (2021.01) |
| *A61L 9/20* | (2006.01) |
| *B01D 53/00* | (2006.01) |
| *F24F 8/10* | (2021.01) |

(52) U.S. Cl.
CPC .................. *F24F 8/22* (2021.01); *A61L 9/20* (2013.01); *B01D 53/007* (2013.01); *B01D 53/04* (2013.01); *F24F 8/10* (2021.01); *A61L 2209/12* (2013.01); *A61L 2209/14* (2013.01); *A61L 2209/16* (2013.01); *B01D 2253/102* (2013.01); *B01D 2253/106* (2013.01); *B01D 2253/202* (2013.01); *B01D 2257/504* (2013.01); *B01D 2257/91* (2013.01); *B01D 2259/4508* (2013.01); *B01D 2259/4575* (2013.01); *B01D 2259/804* (2013.01)

(58) Field of Classification Search
CPC . A61L 9/20; B01D 53/00; B01D 53/04; F24F 8/10; F24F 8/22
See application file for complete search history.

(56) References Cited

U.S. PATENT DOCUMENTS

| 7,914,758 B2 | 3/2011 | Murray et al. |
| 8,772,744 B1 | 7/2014 | Liu |
| 2007/0158499 A1 | 7/2007 | Whittingham |
| 2016/0271289 A1* | 9/2016 | Duffy ........................ A61L 9/20 |
| 2021/0010693 A1* | 1/2021 | Gamroth .................. F24F 11/64 |

OTHER PUBLICATIONS

Foarde, et al; "Biological inactivation efficiency by HVAC In-Duct UV light systems"; Technology Evaluation Report, 2006; (24 pages).
Bosbach, et al; "Evaluation of Cabin Displacement Ventilation under Flight Conditions"; 28th International Congress of the Aeronautical Sciences; Apr. 2013; (11 pages).
Reed; "The History of Ultraviolet Germicidal Irradiation for Air Disinfection"; Public Health Rep; Jan.-Feb. 2010; (24 pages).

* cited by examiner

Primary Examiner — Sharon Pregler
(74) Attorney, Agent, or Firm — K&L Gates LLP

(57) ABSTRACT

An HVAC system is provided. The HVAC system includes a UV light source configured to disinfect air, a ventilation system, and an adsorption filter. The adsorption filter is configured to capture carbon dioxide from air.

8 Claims, 6 Drawing Sheets

ADSORPTION FILTER, VENTILATION SYSTEM AND HVAC SYSTEM HAVING THE SAME

CROSS REFERENCE TO RELATED APPLICATION

The present application claims priority to U.S. Provisional Patent Application No. 63/012,597, filed Apr. 20, 2020, the disclosure of which is incorporated into this specification by reference in its entirety.

BACKGROUND

The current state-of-the-art in the air circulation system in most commercial airlines, cruise ships and metros follows mixed air ventilation system in which cold air is supplied from the roof of the cabin (over the head of the passenger), and then the air is sucked or extracted out at the bottom of the cabin (at the feet of the passengers). This approach encourages spread of infections in case a passenger with infectious disease is onboard the airplane, metro, cruise ship and/or building. For example, Cold air from the aircraft air-conditioning system is supplied from the top, cools down the passengers and then collected at the feet of the passengers. Having cooled down the passengers, the air becomes warm, and from ideal gas law, warm air is lighter and it is expected to travel to the top naturally. As a result, at least some air will escape the suction system at the feet of the passengers, travels to the top and then spreads to other parts of the cabin. Therefore, it may cause issues such as spread of harmful microbes, virus such as coronavirus (COVID-19) through Heating, Ventilation, and Air Conditioning (HVAC) systems, high concentration of $CO_2$ inside the cabin environment which leads to sick building syndrome, and cross-contamination of infectious diseases among passengers especially onboard the airplane, metro, and/or cruise ship.

SUMMARY

The present disclosure generally relates to an adsorption filter, a ventilation system and an HVAC system having the adsorption filter and ventilation system.

In light of the present disclosure, and without limiting the scope of the disclosure in any way, in an aspect of the present disclosure, which may be combined with any other aspect listed herein unless specified otherwise, an HVAC system is provided. The HVAC system includes a UV light source configured to disinfect air, a ventilation system, and an adsorption filter. The adsorption filter is configured to capture carbon dioxide from air.

In an aspect of the present disclosure, which may be combined with any other aspect listed herein unless specified otherwise, the UV light source is provided between an air intake and a plenum.

In an aspect of the present disclosure, which may be combined with any other aspect listed herein unless specified otherwise, the UV light source is configured to disinfect s biological agent in air.

In an aspect of the present disclosure, which may be combined with any other aspect listed herein unless specified otherwise, the adsorption filter includes one or more of polymers, carbon-based materials, silicate-based material, and nanomaterials.

In an aspect of the present disclosure, which may be combined with any other aspect listed herein unless specified otherwise, the HVAC system is provided in at least one of an aircraft, a ship, a train, a vehicle or a building.

In an aspect of the present disclosure, which may be combined with any other aspect listed herein unless specified otherwise, the ventilation system includes an air supply opening and an air extraction opening.

In an aspect of the present disclosure, which may be combined with any other aspect listed herein unless specified otherwise, the air supply opening is provided in a position lower than the air extraction opening.

In an aspect of the present disclosure, which may be combined with any other aspect listed herein unless specified otherwise, the air supply opening is provided on bottom or sides of a cabin of an aircraft, and the air supply opening is configured to supply the disinfected air from the bottom or the sides of the cabin.

In an aspect of the present disclosure, which may be combined with any other aspect listed herein unless specified otherwise, the air extraction opening is provided on a roof of the cabin of the aircraft, and the air extraction opening is configured to extract air out of the cabin.

The reader will appreciate the foregoing details, as well as others, upon considering the following detailed description of certain non-limiting embodiments including an adsorption filter, a ventilation system and an HVAC system having the adsorption filter and ventilation system according to the present disclosure.

BRIEF DESCRIPTION OF THE DRAWING

Features and advantages of the systems and methods described herein may be better understood by reference to the accompanying drawing in which.

Figure 1:
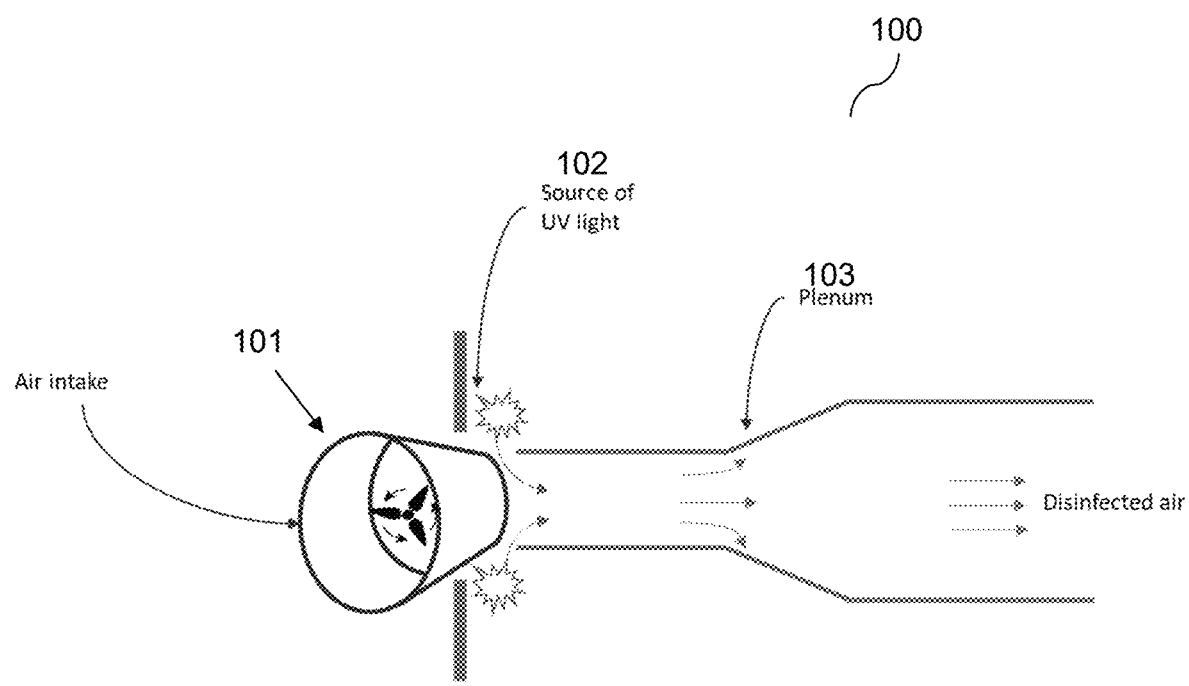
FIG. 1 is a schematic illustration of an HVAC system according to an embodiment of the present disclosure.

The reader will appreciate the foregoing details, as well as others, upon considering the following detailed description of certain non-limiting embodiments according to the present disclosure.

DETAILED DESCRIPTION

The present disclosure generally relates to an adsorption filter, a ventilation system and an HVAC system having the adsorption filter and ventilation system.

The embodiments are described more fully hereinafter with reference to the accompanying drawings, in which some, but not all embodiments of the present technology are shown. Indeed, the present technology may be embodied in many different forms and should not be construed as limited to the embodiments set forth herein.

Likewise, many modifications and other embodiments of the adsorption filter, the ventilation system and the HVAC system described herein will come to mind to one of skill in the art to which the invention pertains having the benefit of the teachings presented in the foregoing descriptions and the associated drawings. Therefore, it is to be understood that the present disclosure is not to be limited to the specific embodiments disclosed and that modifications and other embodiments are intended to be included within the scope of the appended claims. Although specific terms are employed herein, they are used in a generic and descriptive sense only and not for purposes of limitation.

Throughout the specification and claims, terms may have nuanced meanings suggested or implied in context beyond an explicitly stated meaning. Likewise, the phrase "in an embodiment" as used herein does not necessarily refer to the same embodiment or implementation and the phrase "in another embodiment" as used herein does not necessarily refer to a different embodiment or implementation. It is intended, for example, that claimed subject matter includes combinations of exemplary embodiments or implementations in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" or "at least one" as used herein, depending at least in part upon context, may be used to describe any feature, structure, or characteristic in a singular sense or may be used to describe combinations of features, structures or characteristics in a plural sense. Similarly, terms, such as "a", "an", or "the", again, may be understood to convey a singular usage or to convey a plural usage, depending at least in part upon context. In addition, the term "based on" or "determined by" may be understood as not necessarily intended to convey an exclusive set of factors and may, instead, allow for existence of additional factors not necessarily expressly described, again, depending at least in part on context.

The terminology used herein is for the purpose of describing particular example embodiments only and is not intended to be limiting. The terms "comprise", "comprises", "comprised" or "comprising", "including" or "having" and the like in the present specification and claims are used in an inclusive sense, that is to specify the presence of the stated features but not preclude the presence of additional or further features.

A large proportion of sick building syndrome (SBS) emanates from conditioned air through the HVAC systems, especially due to the accumulation of microbes on the cooling coils or passage of microbes along the duct and plenum. The SBS is identified as ill health symptoms that are associated with; asthma symptoms (e.g. wheezing), mucous membrane irritation (e.g. sore throat and nasal congestion), gastrointestinal disturbances, neurotoxic effect (fatigue and headache), sensitivity to odors, and dry skin. Moreover, severe toxicosis and cancer have also been linked to continuous exposure to mycotoxin in HVAC systems. It is now becoming rampant to have these symptoms appeared among occupants in school buildings, office buildings, hospitals, recreational facilities and public buildings. If the symptoms persist in most cases, it often leads to the closure of the facility. The consensus points to the designs of the buildings, which are made airtight for energy-saving purposes—windows stay shut, devoid of daylighting and natural ventilation, and HVAC systems continue to recirculates the same air, with small percentage of fresh air-makeup. As with many known SBS, it is difficult to classify the causative agents into biological, physical, chemical or psychogenic in nature. With biological causative agents such as viruses and bacteria, for example, the rate and severity of COVID-19 spread have awakened researchers in the built environment to take further steps to improve indoor air quality.

It is reported that transmission of coronavirus can occur even when there is no physical contact with infected/contaminated persons or fomites. This shows that, to some extent, the coronavirus can be contracted through contaminated air, especially in buildings, airplanes, metros, or cruise ship where the percentage of fresh air-makeup is very small. With chemical causative agents, there have been reports that high concentration of $CO_2$ in an enclosed space is responsible for wheezing attacks in children with asthma history, tiredness and muscular pains, increase in airborne bacterial markers, sicknesses (cough, headache, rhinitis, wheezing and irritation of mucus membrane), especially where air circulation may be poor.

The present disclosure discloses at least the following aspects: (1) an HVAC system having a UV light device configured to irradiate UV spectrum in the plenum of the HVAC system of the airplanes, metros, trains, and/or cruise ships to disinfect the air of biological agents such as coronavirus; (2) a ventilation system that is provided inside the airplanes, metros, trains, and/or cruise ships to provide disinfected air from bottom and/or sides of a cabin or space in a bottom-up manner; (3) an adsorption filter that is configured to disinfect and absorb $CO_2$ from the air before it is sent to the passengers and/or occupants.

FIG. 1 is a schematic illustration of a UV light as a disinfectant in an HVAC system according to an embodiment of the present disclosure. For example, the HVAC system 100 includes a UV light source configured to disinfect air, a ventilation system configured to supply and circulate air. As illustrated in FIG. 1, ambient air in an airplane/metro/ship is taken into the plenum 103 from an air intake 101 of the HVAC system 100. The UV light source 102 may be but not limited to a non-linear UV light source. Other types of UV light source is desirable as well. The UV light source 102 is positioned between the air intake 101 and the plenum 103. The UV light source 102 serves two purposes: (1) to disinfect the incoming air, and (2) to disinfect the inner surface of the duct in order to deactivate any possible microbial growth in the ventilation system. The UV light source 102 provides incident UV light on or along the duct within the range of wavelengths (220-300 nm) and works effectively as a disinfectant. The irradiance is controlled to reach all the crannies in order to avoid creating dark side, which would create hotspots for microbial growth. The disinfected clean air is then supplied to cabins or rooms of the airplanes, metros, trains, cruise ships, and/or buildings.

Figure 2:
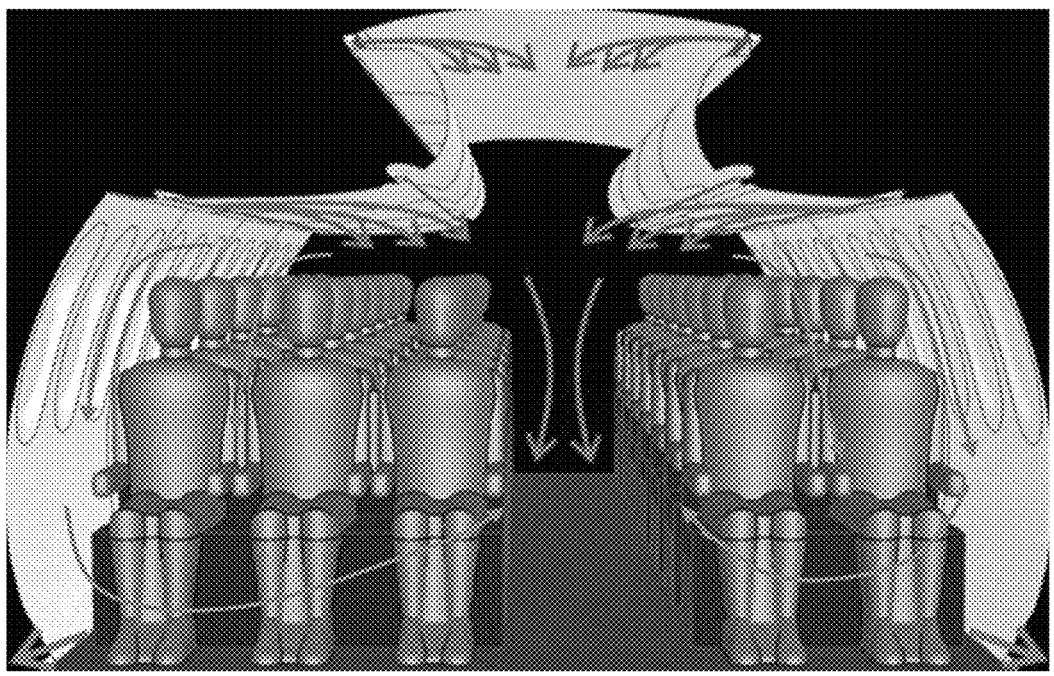
FIG. 2 is an illustration of a conventional ventilation system in an aircraft.

FIG. 2 illustrates a conventional ventilation system in an aircraft. The conventional ventilation system inside the commercial airplane cabin is designed for the passengers to receive fresh air from the top (over the head of the passenger), and then the air is sucked or extracted at the bottom (at the feet of the passengers). This approach encourages spread of infections in case a passenger with infectious disease such as coronavirus is onboard the airplane.

Cold air from the conventional ventilation system in the aircraft (see FIG. 3) is supplied from the top, cools down the passengers and it is collected at the feet of the passengers. Having cooled down the passengers, the air becomes warm, and from ideal gas law, warm air is lighter and it is expected to travel to the top naturally. As a result, a part of the air will escape the suction system at the feet of the passengers, travels to the top and then spreads to other parts of the cabin.

Figure 3:
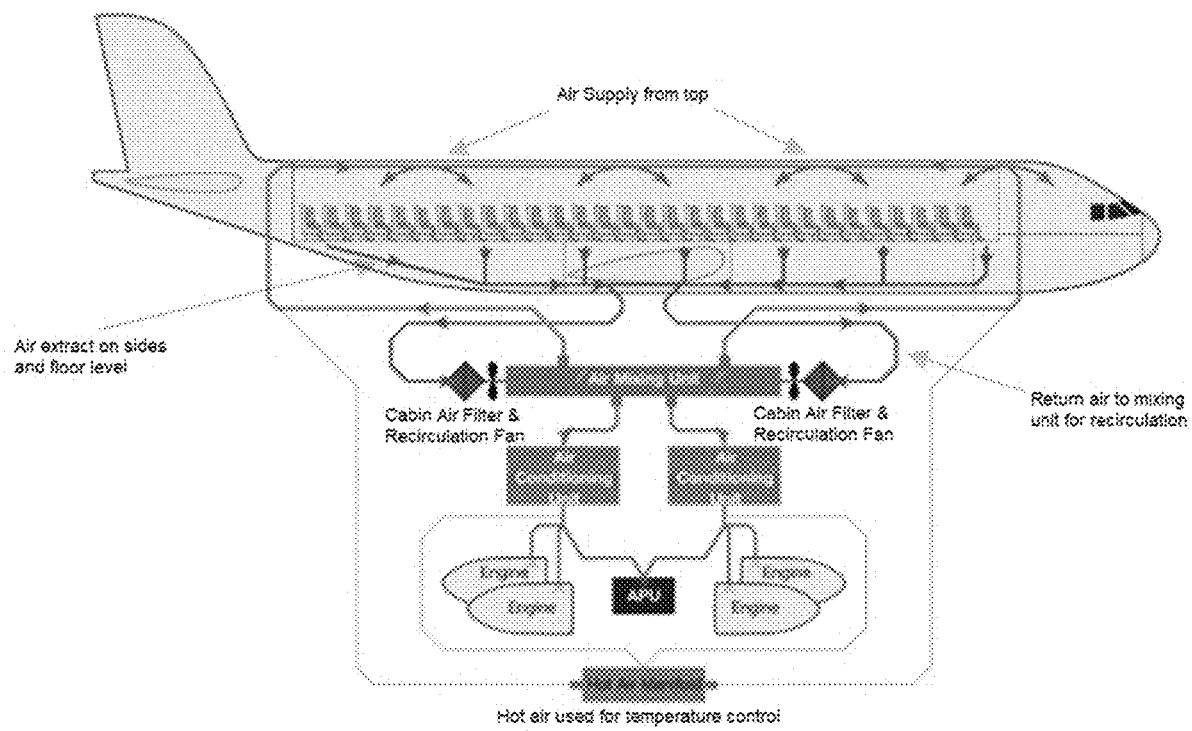
FIG. 3 is a schematic illustration of the conventional ventilation system in the aircraft as illustrated in FIG. 2.

According to an embodiment of the present disclosure, a ventilation system is provided to supply disinfected air from bottom, sides and/or floor level of a cabin or space in a bottom-up manner. The ventilation system follows ideal gas law, in which warm air is lighter than cold air and would always prefer to go up in a relatively cold environment. As a result, it is better than the conventional ventilation system as illustrated in FIG. 3, which forces warm air to the feet of the passengers against natural convection.

Figure 4:
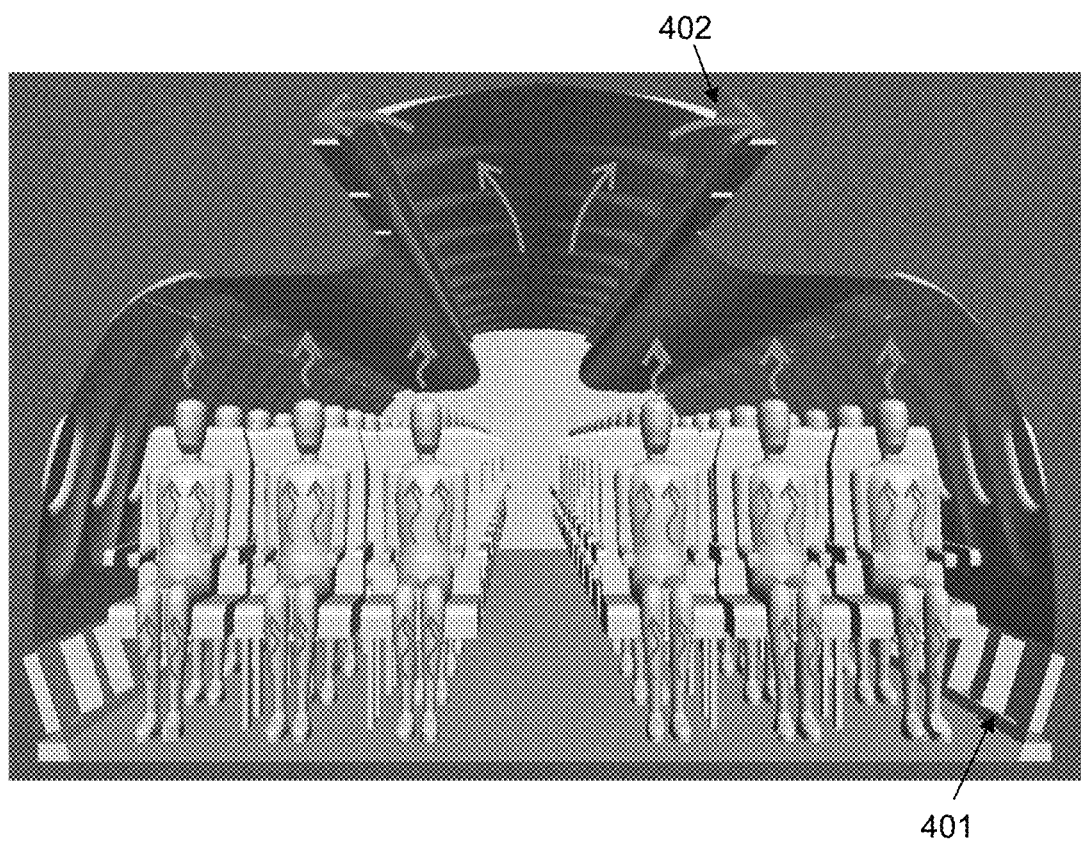
FIG. 4 is an illustration of a ventilation system in an aircraft according to an embodiment of the present disclosure.

FIG. 4 illustrates a ventilation system in an airplane according to an embodiment of the present disclosure. For example, the ventilation system includes air supply openings 401 and air extraction openings 402. The air supply openings 401 are provided in a position lower than the air extraction openings 402. For example, the air supply openings 401 are provided on sides, bottom and/or floor level of a cabin or room of the airplanes. The air extraction openings 402 are provided on the top or the roof of the cabin or room of the airplanes. The ventilation system can be applied or used in metros, trains, cruise ships, and/or buildings as well according to another embodiment of the present disclosure.

Figure 5:
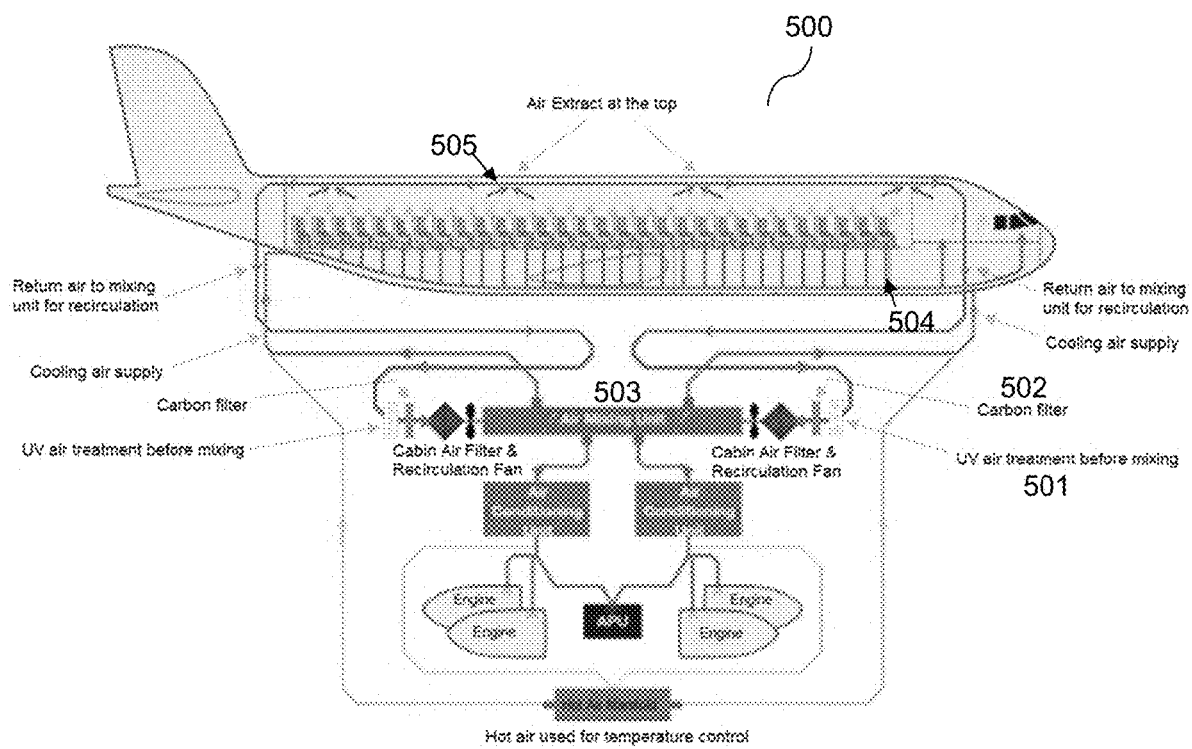
FIG. 5 is a schematic illustration of a ventilation system in an aircraft according to an embodiment of the present disclosure.

FIG. 5 is a schematic illustration of a ventilation system in an aircraft according to an embodiment of the present disclosure. As illustrated in FIG. 5, disinfected fresh air is firstly supplied from air supply openings 504 at the bottom or sides of the cabin, cools down the passengers and it is then collected by air extraction openings 505 at the top or on the roof of the cabin. At the point of collection of used air at the upper roof of the cabin, an Ultraviolet Germicidal Irradiation (UVGI) will be stationed there to deactivate any microbe therein. Another UVGI 501 is placed before the air mixing unit 503 as shown in FIG. 5. With this arrangement, any microbe or virus that escapes the first treatment at the roof of the cabin will be effectively deactivated before the air mixing unit 503. An air filter 502 is further provided between a recirculation fan and a UV air treatment device such as UVGI 501. The air filter 502 may include but not limited to one or more of polymers, carbon-based materials, silicate-based material, and nanomaterials.

In order to reduce the spread of virus such as COVID-19 and other harmful microbes through the HVAC systems, to enhance indoor air quality by deactivating harmful biological and chemical agents, to reduce cross-contamination of infectious diseases, to reduce the concentration of $CO_2$ in indoor atmosphere and stop the sickness that is associated with traveling through the air, the present disclosure discloses an HVAC system having an adsorption filter.

Figure 6:
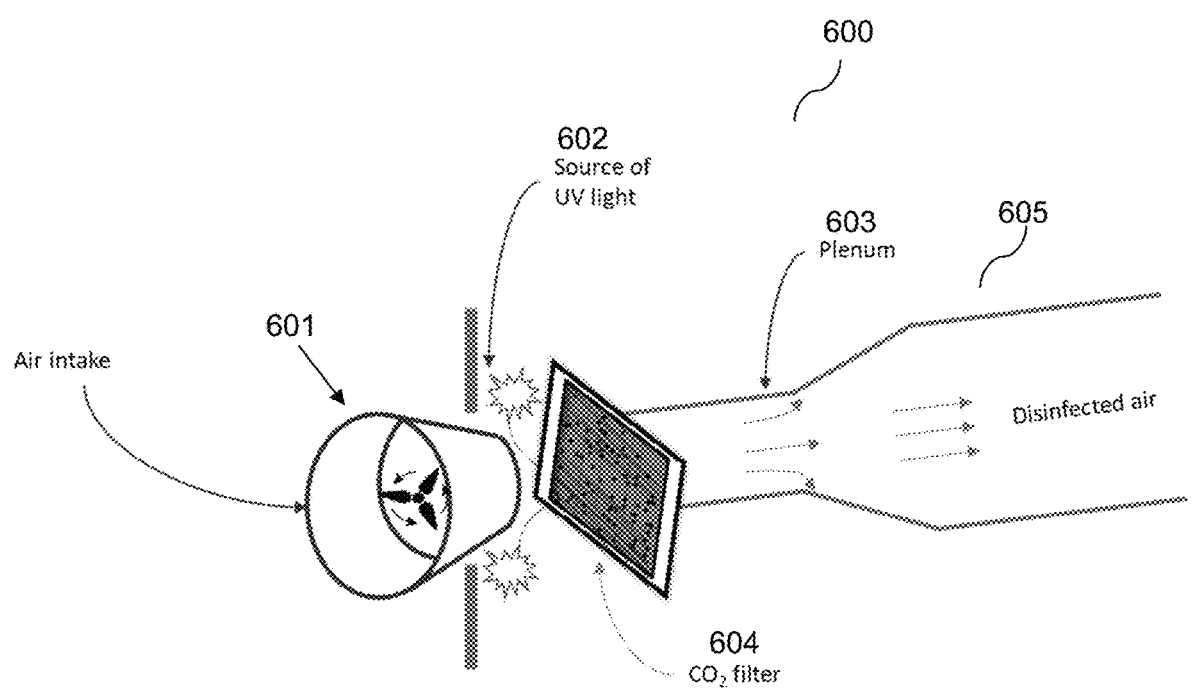
FIG. 6 is a schematic illustration of an HVAC system according to an embodiment of the present disclosure.

FIG. 6 illustrates an HVAC system having a $CO_2$ adsorption filter and a UV light source according to an embodiment of the present disclosure. For example, the HVAC system 600 includes a UV light source 602 configured to disinfect ambient air, a $CO_2$ adsorption filter 604 configured to reduce the concentration of $CO_2$, and a ventilation system 605 configured to supply and circulate disinfected air. The UV light source 602 may be but not limited to a non-linear UV light source. Other types of UV light source is desirable as well. The air intake includes a fan 601. The UV light source 602 is provided between the air intake fan 601 and the plenum 603 to disinfect the incoming air and the inner surface of the plenum 603 in order to deactivate any possible microbial growth in the ventilation system 605. The UV light source 102 provides incident UV light on or along the duct within the range of wavelengths (220-300 nm) and works effectively as a disinfectant. The irradiance is controlled to reach all the crannies in order to avoid creating dark side, which would create hotspots for microbial growth.

After the air is treated and disinfected by the UV light source such as an UVGI, the disinfected air passes through the $CO_2$ adsorption filter 604. The $CO_2$ adsorption filter 604 is a filter treated with adsorbents capable of selectively capture $CO_2$ from the air stream at ppm level. For an indoor or closed environment, which is relatively cold due to the HVAC system, the system will benefit from low temperature (18-22° C.) for adsorption of $CO_2$ from the used air.

The $CO_2$ adsorption filter may be selected from a number of materials such as but not limited to polymers, carbon, fabric, felt, silicate based, polypropylene based materials, silicate-based material. The material is modified using nanomaterials (e.g. carbon nitride or metal-organic frameworks, MOFs and/or nanoscale faujasite, FAU) that have high $CO_2$ absorptive capability. The adsorbent materials will be either grafted onto the filter materials or pelletized to be added as a second media layer. The grafting/coating of the adsorbent materials onto the filter material will follow a gas-injection approach. For example, the adsorbent materials are selectively heated and thermally fused to the filter material matrix through spraying. This ensure strong adherence to the filter when cooled. The pellets formed from the adsorbent materials are shaped and conditioned in a way to minimize pressure drop when used in the HVAC system.

According to an embodiment of the present disclosure, an HVAC system rerouting the conventional air circulation system in the airplane, metro, train, ship, and/or building is provided. For example, the HVAC system displace conventional ventilation system, places UV light source(s) at the roof of airplane cabin or metro tube where the used air is collected, and then beams the UV light at a wavelength between 220-300 nm to deactivate any microbe therein. The HVAC system may also place the UV light source(s) at or near the air mixing chamber to further deactivate any microbe that escapes to the mixing chamber. The HVAC system further includes a filter. The filter includes a filter material that is treated with nanomaterials or the like via coating or thermal fusion. The filter is placed after the UV light source at the roof of the airplane cabin or metro tube in order to adsorb the $CO_2$ in the used air. The filter may also be placed at or near the air mixing chamber to further reduce the $CO_2$ concentration.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An HVAC system, comprising:
a UV light source configured to disinfect air,
a ventilation system including an air supply opening and an air extraction opening, and
an adsorption filter,
wherein the adsorption filter is configured to capture carbon dioxide from air, and
wherein the air supply opening is provided on at least one of a bottom or a side of a cabin of an aircraft, and the air supply opening is configured to supply the disinfected air from the at least one of the bottom or the side of the cabin.

2. The HVAC system according to claim 1, wherein the UV light source is provided between an air intake and a plenum.

3. The HVAC system according to claim 1, wherein the UV light source is configured to disinfect biological agent in air.

4. The HVAC system according to claim 1, wherein the UV light source is configured to disinfect virus in air.

5. The HVAC system according to claim 1, wherein the adsorption filter includes one or more of polymers, carbon-based materials, silicate-based material, and nanomaterials.

6. The HVAC system according to claim 1, wherein the HVAC system is provided in at least one of an aircraft, a ship, a train, a vehicle or a building.

7. The HVAC system according to claim 1, wherein the air supply opening is provided in a position lower than the air extraction opening.

8. The HVAC system according to claim 1, wherein the air extraction opening is provided on a roof of a cabin of an aircraft, and the air extraction opening is configured to extract air out of the cabin.

* * * * *